United States Patent [19]

Heitz et al.

[11] Patent Number: 4,750,143

[45] Date of Patent: Jun. 7, 1988

[54] APPARATUS FOR THE RAPID DETERMINATION OF THE MOISTURE CONTENT OF A MATERIAL

[75] Inventors: Georges Heitz, Montigny les Metz; Bernard Boury, Metz; Jean Philippe, Kedange, all of France

[73] Assignee: Institut de Recherches Siderurgie Francaise, Maizieres les Metz, France

[21] Appl. No.: 830,228

[22] Filed: Feb. 18, 1986

[51] Int. Cl.⁴ .................... G01G 7/16; G01N 5/02; G01R 27/26

[52] U.S. Cl. .................... 364/556; 364/567; 73/76; 324/61 R; 177/25

[58] Field of Search ............ 364/496, 497, 550, 551, 364/567, 556; 177/25.11, 25.13, 25.18, 25.19, 164, 165; 131/299, 303; 73/73, 76, 29; 219/10.55 R; 324/61 R; 264/40.4

[56] References Cited

U.S. PATENT DOCUMENTS

| | | | |
|---|---|---|---|
| 3,909,598 | 9/1975 | Collins et al. | 364/567 |
| 3,978,325 | 8/1976 | Goldstein et al. | 364/557 X |
| 4,165,633 | 8/1979 | Raisanen | 364/556 X |
| 4,168,623 | 9/1979 | Thomas, Jr. | 364/497 X |
| 4,316,384 | 2/1982 | Pommer et al. | 364/567 X |
| 4,485,284 | 11/1984 | Pakulis | 73/73 X |
| 4,651,285 | 3/1987 | Collins et al. | 73/76 X |

Primary Examiner—Parshotam S. Lall
Assistant Examiner—Joseph L. Dixon
Attorney, Agent, or Firm—Wm. J. Kopacz

[57] ABSTRACT

A device for determining the moisture content of a material which includes a micro wave heating unit (1) for heating a sample of the material which is under investigation and a weighing device (3) for weighing the sample during heating and providing signals representing a series of measurements of the weight of the sample at specific times. The weighing device is connected to a processing unit (4) which is a microprocessor and which includes a computer (9) which produces signals representing the loss of weight of the sample in the course of heating and which computes the parameters of a asymptotic function and which represents the loss of weight of the sample in the course of time. There is also a calculator (11) for determining the differences between two asymptotic values, and a comparator (12) for comparing the differences with a reference value representing the acceptable uncertainty in regard to the moisture content of the material. There is also a restoring device for restoring the asymptotic values when the differences reach values which are equal to or less than the reference value.

3 Claims, 1 Drawing Sheet

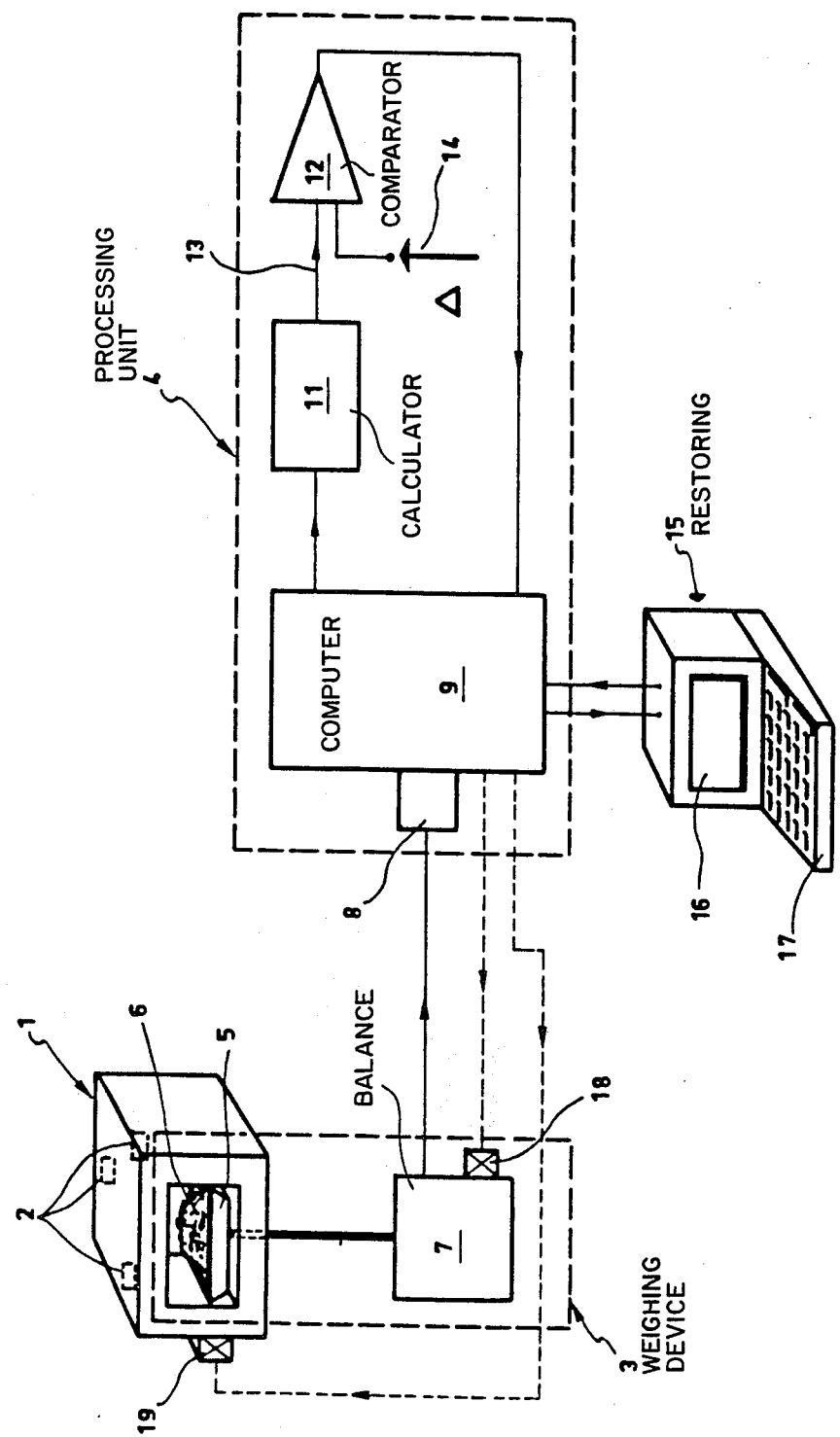

APPARATUS FOR THE RAPID DETERMINATION OF THE MOISTURE CONTENT OF A MATERIAL

FIELD OF THE INVENTION

The present invention relates to an apparatus for the determination of the moisture content of a material, more especially coke intended to be fed to a blast furnace.

BACKGROUND OF THE INVENTION

Different apparatuses are currently known, which are capable of determining the moisture content of a material; these apparatuses may be classified schematically in two groups, according to whether the measurement is made on a continuous or discontinuous basis.

Among the apparatuses falling within the first group, it is possible to mention, for example, neutron probes and retrodiffusion probes. These permit results to be obtained rapidly, but their lack of accuracy at low moisture content levels and their sensitivity to the surrounding medium limit their use considerably.

In the second group, mention will principally be made of the apparatuses making use of weight measurement methods, in which an operation of heating a sample is followed by a weighing operation. (U.S. Pat. No. 4,168,623, U.S. Pat. No. 3,909,598, JP-A No. 58-162839 for ex.) These apparatuses give satisfactory results, but the drying time is long and becomes further extended with increasing initial moisture content of the material under investigation. Furthermore, for a given moisture content range and a given weight of material, there is an optimum drying power, beyond which the period of time required for drying does not diminish any further.

Finally, these apparatuses are not suitable for carrying out rapid measurements.

OBJECT OF THE INVENTION

The object of the present invention is to avoid the above indicated disadvantages. More especially, the object of the invention is to provide an apparatus which is capable of determining the moisture content of a material rapidly and with accuracy by measurements of the weight of a sample.

SUMMARY OF THE INVENTION

The invention relates to an apparatus for the determination of the moisture content of a material, the said apparatus including:

a chamber for heating a sample of the material under investigation, of known mass Mo, a device for weighing the sample in the course of heating, such device including a means for supporting the sample, a processing unit which is connected to the weighing device in such a manner as to receive signals $M_j{}^i$ representing a series i of measurements of the weight of the sample at specific times $t_j$, such unit comprising:

a computer for converting the signals $M_j{}^i$ into signals $Y_j{}^i$ representing the loss of weight of the sample in the course of heating and computing, with the aid of the pairs of associated values $[Y_j{}^i, t_j]$, the n parameters of a general function $f_n(t)$ which is asymptotic with respect to t and which represents the loss of weight of the sample in the course of time and for computing the asymptotic value $A^i$ which is adopted by the specific function $f_n{}^i(t)$ when t tends towards infinity;

a calculator for computing the differences $\delta^{i,i+1}$ between two successive asymptotic values $A^i$ and $A^{i+1}$ emanating from the series of measurements i and i+1;

a comparator for comparing the differences $\delta^{i,i+1}$ with a reference value $\Delta$ representing the acceptable uncertainty regarding the determination of the moisture content of the material under investigation;

and means for restoring the asymptotic values where the differences $\Delta$ reach values which are equal to or less than the reference value.

Preferably, the apparatus according to the invention further comprises means permitting the automatic termination of the heating of the sample and of the measurements of the weight of the sample as soon as the difference $\delta^{i,i+1}$ between two successive asymptotic values $A^i$ and $A^{i+1}$ is less than or equal to the preset value $\Delta$ which has been made applicable.

In a preferred embodiment, the heating chamber is a microwave oven.

According to an advantageous embodiment, the processing unit is constituted by a microprocessor assembly provided with an analog/digital converter, the input of which is connected with the weighing device.

The apparatus according to the invention is capable of rapidly giving an accurate value of the moisture content of a material by carrying out no more than partial drying, or even only initial drying, of a sample of the material under investigation.

The inventors utilized their knowledge in the field of drying, and of the asymptotic development of the weight of a material heated by microwaves, to develop apparatus capable of restoring the moisture content value of such material in reliance upon a limited number of weight measurements taken in the course of the drying process, or even only at the start of the drying operation.

The apparatus according to the invention can be provided with a processing unit suitable for carrying out the rapid processing of the measurements of the weight of the sample in the course of the drying process by a technique of numerical analysis, for example the technique which applies the well known method referred to as the method of "least squares". In this case, such processing consists, first of all, in introducing a first series i of l pairs of values "$y_j{}^i$, $t_j$" into the relation:

$$E^i = \sum_{j=1,1} (y_j^i - y_{jc}^i)^2$$

where $Y_{jc}{}^i$ represents the theoretical moisture content of the sample under investigation at time $t_j$.

An attempt to find a extreme value of this function $E^i$ permits determination of the n parameters of the specific function $Y^i = f_n{}^i(t)$, and thus the formulation of a first drying equation, on the basis of which a calculation is made, in a simple manner and under conditions in which the variable t (drying time) tends towards infinity, of its asymptotic value $A^i$, which represents a first value of the moisture content of the material under investigation. Subsequently, by introducing a new series (i+1) of l pairs of "loss of weight—time" values found for example following the l preceding ones, the computing unit proceeds, in the same manner as previously, to determine a new specific drying function $y^{i+1} = f_n{}^{i+1}(t)$ and then its asymptotic value $A^{i+1}$, it being understood that l is an integer at least equal to the number n of parameters of the function $f_n(t)$.

The invention is likewise applicable to the case where the l pairs of "loss of weight—time" values of the series of measurements $i+1$ overlap partially with the l pairs of the preceding series i.

Indeed, the overlap between two successive series of l pairs of "loss of weight—time" values is preferably such that, in order to form the following series, one or more pairs of values corresponding to the shortest drying times are deleted from the previous series and an equal number of pairs of values taken at subsequent times is added to the series of the l previous pairs.

Finally, as soon as the asymptotic values have stabilised, that is to say as soon as the successive asymptotic values no longer vary among themselves by more than a certain difference value $\Delta$ which is adopted as a criterion, the processing unit restores the last asymptotic value or values which satisfy the test and which, as has been stated previously, represent the moisture content of the material under investigation.

One of the principal advantages of the invention resides in the time savings achieved in comparison with traditional drying apparatuses, as well as in the accuracy of the determination of the moisture content, it being understood that such accuracy is associated with the reference value for the difference $\Delta$ which has been adopted.

Furthermore, the combination of the operations of drying and weighing the sample, which is carried out with the apparatus according to the invention, an apparatus suitable for continuously measuring the moisture content, such apparatus minimising the operations of handling the samples under investigation as well as the risks of error which may, for example, arise as a result of losses of material.

Accordingly, the apparatus according to the invention is particularly suitable for carrying out measurements in series.

BRIEF DESCRIPTION OF THE DRAWING

The invention will be properly understood, and other advantages and characteristics will appear more clearly, with reference to the description which will follow and which is given with reference to the single accompanying drawing, which schematically represents an apparatus according to the invention.

SPECIFIC DESCRIPTION

The example illustrated relates to the determination, by means of microwave heating, of the moisture content of a sample of metallurgical coke, for example at the outlet of a coke oven works or before supply thereof to a blast furnace.

The sample of coke is heated in the chamber of a microwave oven 1, which is connected to an external electricity supply (not shown), the said chamber being provided, in its upper part, with sources which emit microwaves (magnet) and which are represented at 2.

Each one of these sources traditionally comprises an ultra-high frequency generator associated with a waveguide; these have not been shown, in order to avoid unnecessarily overcrowding the FIGURE.

The oven 1 is preferably provided, in its upper part, with three sources 2 disposed on a circle at 120° from one another. This arrangement offers the advantage of permitting homogeneous distribution of the microwave radiation throughout the volume of the oven.

According to the invention, the oven 1 is associated with a weighing device 3, which is itself connected to a processing unit 4 interactively connected with a visual display unit 15.

The weighing device 3 includes a plate 5 which is located in the oven 1 and which is intended to support the sample 6 of metallurgical coke throughout the duration of exposure thereof to the microwaves. A balance 7 which is located outside the oven 1 and which is directly connected to the plate 5 completes the weighing device 3.

The plate 5 is preferably chosen to be of a material inert to microwaves, for example of glass, as "Pyrex" ®. Other materials, such as aluminium-based alloys, may also be suitable. But, materials containing iron should be avoided, since a particular feature of such materials is that they reflect microwaves.

The weighing device 3 is connected to the processing unit 4, which thus receives at its input the signals representing the pairs of "weight measurement—drying time" values, which is represented by $(M_j^i, t_j)$.

In the example under consideration, a clock 8 permits sampling of the measurements, by imposing a time interval $\Delta t$ between each pair of $(M_j^i, t_j)$ values taken into account for processing purposes.

The processing unit 4 is constituted in the following manner:

the sampled pairs $(M_j^i, t_j)$ are first received by a high speed computer 9 which registers the data after having converted them into digital form by means of a built-in analog/digital converter. This computer has three essential functions. The first is to convert the pairs $(M_j^i, t_j)$ into pairs $(Y_j^i, t_j)$ where $Y_j^i$ represents the relative loss of weight of the sample due to evaporation of moisture under the influence of the microwaves. In order to do this, the computer takes account of the relation (I):

$$Y_j^i = 100 \frac{(Mo - M_j^i)}{Mo},$$

which expresses $Y_j^i$ in terms of percentages by weight and in which Mo represents the initial weight of the sample, before exposure thereof to the microwaves.

The computer 9 also contains the general equation (II), $Y = f_n(t)$ for n parameters, this equation representing a family of curves which are asymptotic with respect to the axis of the times t. Thus, starting from the series i of pairs $Y_j^i$, $t_j$, the second essential function of the computer consists in determining the specific drying function $Y^i = f_n^i(t)$ by computing the n parameters by resolving a linear system of n equations with n unknowns. Once this specific function $f_n^i(t)$ has been determined, the third essential role of the computer is to ascertain the asymptotic value $A^i$ of $f_n^i(t)$, simply by computing the value which is adopted by $Y^i$ as t tends to infinity.

These operations are repeated for other series of measurements $i+1$, $i+2$, etc.

The values of the asymptotes are compared among themselves by formulating the successive differences of the type $\delta^{i+1,i} = |A^{i+1} - A^i|$ which are developed by virtue of computing means which are schematically represented at 11. A comparator 12 then receives at its input 13 the differences $\delta^{i+1,i}$ which it compares with a reference value $\Delta$ which is not to exceed what it receives at another input 14.

Means 15 for restoring the results, i.e. the values $A^i$ validated by the test imposed in the comparator 12, complete the apparatus according to the invention.

Now, as soon as the asymptotic values $A^i$ which have been computed are stable, that is to say when at least two values $A^i$ no longer vary among themselves beyond the reference value $\Delta$ the restoration of these values $A^i$ is effected by means of the processing unit 4.

Preferably, two positive tests, that is to say three successive asymptotic values for which the differences $\delta^{i+1,i}$ are less than $\Delta$, cause the restoration of the results.

Likewise, it will be preferable for the last value $A^i$ to be accepted as being the degree of moisture content of the material under investigation.

These restoring means 15 include a display screen 16 connected to the unit 4, as well as by a keyboard 17 permitting dialogue interaction with this unit and, if necessary, modification of the data, for example the reference value for the difference $\Delta$, the general function $f_n(t)$ or indeed the interval $\Delta t$ driving the clock 8.

Furthermore, the apparatus shown by way of example in the drawing includes devices 18 and 19, which control the arrest of the weighing device 3 and of the oven 1 respectively and which are automatically actuated by the processing unit 4 at the time of the validation of the asymptotic values $A^i$.

The range of functions which are desired for the processing unit 4 and which have just been described may advantageously be executed with the aid of a commercial microprocessor, for example by the microprocessor marketed by the firm INTEL under reference number 8088 or 8086.

The detailed description of the operation of the apparatus which follows will permit better appreciation of the advantages of the invention.

As has been stated previously, the example presented relates more particularly to the analysis of the moisture content of metallurgical coke by means of microwaves.

The studies carried out in this area by the inventors have made it possible to show that a general function $f_n(t)$ of asymptotic form (III):

$$\sum_{m=1,p} K_m [1 - \exp(t - \tau) \cdot L_m],$$

(in which $K_m$, $\tau$, $L_m$ are parameters which adopt constant values specific to each batch of coke which is investigated), provides an accurate indication of the development of the loss of weight of a sample of coke as a function of the time t of exposure to the microwaves, it being possible for the index p to be equal to 1, 2 or 3 in dependence upon the degree of moisture content estimated by way of a rough approximation.

The experiments have made it possible to show that in the case of a moisture content by weight which is referred to as low, that is to say less than approximately 2%, the general equation (III) was satisfactory with p=1.

In the case of a greater moisture content, that is to say up to approximately 8%, p=2 is preferably chosen, and in the case of moisture content levels exceeding 8% equation (III) with p=3 gives excellent results.

Depending upon the coke which is being investigated, the operator will thus be at liberty to choose the rank-m general equation which is most appropriate.

The sample of coke which is being investigated is accordingly introduced into the chamber of the microwave oven 1 and deposited on the plate 5. After the sealing of the oven 1, the processing unit 4 commands in the first instance the actuation of the weighing device, which thus proceeds to measure the initial weight Mo of the sample. It is only after this that the oven 1 is actuated, thereby submitting the sample to the action of the microwaves. The development of its weight $M_j{}^i$ is measured continuously by the weighing device 3, which transmits such development to the unit 4 through the regulable clock 8, which ensures sequential recording of the weight measurements.

In this connection, it will be noted that if the first values of moisture content, which are determined in the course of the analysis of a sample with the aid of the apparatus according to the invention, fluctuate among themselves to a significant extent, this means that the series of l values of "loss of weight—drying time" pairs, i.e. "$Y_j{}^i$, $t_j$", are not sufficiently representative of the desired drying curve. In this case one would, for example, increase the $\Delta t$ which has been adopted between each $M_j{}^i$ taken into account for the purposes of the assessment of the moisture content, or the increase the reference value $\Delta$.

Such a fluctuation between the moisture content values which are determined may be found, in particular, in the case of the first measurements, which in fact correspond to the transitional period during which the drying operation is commenced. This fluctuation subsequently disappears rapidly with the subsequent measurement points.

Following this, the unit 4 proceeds with the treatment of the pairs of values ($M_j{}^i$, $t_j$), the general principle of which has been described above.

A specific and detailed example will elucidate with greater precision the processing which is carried out with the pairs of values ($Y_j{}^i$, $t_j$) in the processing unit.

What is involved is a study of a sample of coke having an initial mass Mo equal to 3893.6 g, which is placed in a microwave oven capable of providing a maximum useful power of 3 KW at a frequency of 2450 MHz. In this example, the oven was operated at ¾ of its maximum power.

The interval $\Delta t$, which is set for the clock 8 between each measurement taken into account in the computer 9, is in this instance 3 minutes.

The values of the pairs ($Y_j{}^i$, $t_j$) are indicated in table I presented at the end of the description.

Table II, which is presented thereafter, gives the results obtained by the processing of the values of pairs ($Y_j{}^i$, $t_j$).

The coke investigated is well known as generally having a moisture content by weight exceeding 2% but below 8%.

Consequently, as stated above, the function (III) was employed with p=2, which gives:

$$f_n(t) = K_1[1 - \exp(t-\tau).L_1] + K_2[1 - \exp(t-\tau).L_2]$$

where $K_1$, $K_2$, $L_1$, $L_2$ and $\tau$ are the constants to be determined.

For the determination of $A^i$, that is to say of the asymptote of the drying curve $Y^i = f_n{}^i(t)$, a difference preset value $\Delta$ of 0.1% is adopted, which must be satisfied by three successive asymptotic values among themselves.

The traditional method of the "least squares" permits the formulation, for each series i of measurements which are processed, of a drying equation $Y^i = f_n{}^i(t)$, n being equal to 5 in this example, and determination of the value $A^i$ of its asymptote.

In the present example, the first drying equation and its asymptote were determined by using the first 10 measurements, that is to say after 27 minutes of exposure to the microwaves.

The subsequent processing operations were carried out by making use of the complete series of measurements used in the previous processing operation and some measurements carried out at subsequent times.

Accordingly, the second processing operation takes account of the first 12 measurements; the third processing operation takes account of the first 15 measurements; the fourth processing operation takes account of the first 20 measurements, and the fifth and last processing operation takes account of the first 22 measurements after a total period of one hour of exposure to the microwaves.

The last three asymptotic values determined, which amount to 6.19%, 6.10% and 6.16% respectively, satisfy the required test, that is to say the difference between two successive asymptotic values is—as can be seen—less than $\Delta$, which in this case was fixed at 0.1%.

In this example, a value of 6.16% was finally accepted as being the moisture content by weight of the coke under consideration. This sample was moreover subjected to complete drying by means of microwaves, under the same operational conditions as before. Complete drying was achieved after 91 minutes of exposure, and shows a moisture content by weight amounting to 6.19%, i.e. a value very close to that determined by calculation, which is 6.16%. The gain in time achieved in this case is $\frac{1}{3}$.

Other tests, which were also carried out with samples of metallurgical coke, have shown that:

in the case of cokes referred to as having "low moisture content", that is to say below 2%, if a value of $\Delta$ amounting to 0.1% is chosen the apparatus according to the invention gives, after only the first $\frac{1}{3}$ of the time required for complete drying, results which are as good as those obtained after complete drying of the sample. Thus, a 5 kg sample of coke, which is traditionally dried in 90 minutes by means of microwaves, was analysed in 30 minutes by the apparatus according to the invention;

in the case of cokes referred to as having "a high moisture content", that is to say the moisture content of which is within the range between 2% and 8% by weight, with a value of $\Delta$ of 0.3% the expected results were obtained after a period of time slightly less than one half of the time required for complete drying. Thus, a 5 kg sample of coke, the traditional drying of which by means of microwaves would require 45 minutes, was analysed in 20 minutes with the apparatus according to the invention.

It is clear that the invention limited to the example described, but extends to multiple variants or equivalents.

Accordingly, the invention is not limited to a chamber in which drying is carried out by means of microwaves. It is also possible to envisage a chamber which is heated electrically or in another manner, provided that the loss of weight can be expressed in terms of a model involving an asymptotic function.

Likewise, the general function $f_n(t)$ is not limited to the expressions quoted in the example described hereinabove, and likewise includes all analytical expressions representing a family of asymptotic curves capable of faithfully reproducing the development of the loss of weight of a material as a function of the drying time.

However, in the course of the heating operation it is necessary to avoid a situation in which hot spots are formed on the sample. Otherwise, there is a risk of local combustion, and the loss of weight would no longer be solely associated with loss of moisture. In order to prevent any possible formation of hot spots, it is possible advantageously to provide for sequential operation of the magnetrons or momentary masking of the latter by the blades of a fan, or indeed rotation of the support plate itself, or any other arrangement designed to improve the homogeneity of heating.

Likewise, the invention, which is applicable for the purposes of the analysis of the moisture content of a coke, is similarly applicable for the purposes of the analysis of the moisture content of other materials, more especially carbonaceous materials, for example crude mixtures of sintered materials.

Furthermore, the plate 5 may likewise be replaced by any other support means, for example a conveyor belt which is provided with balances and which moves within a heating chamber 1 of the "tunnel" furnace type for a process of continuous analysis of the moisture content.

TABLE I

| $t_j$ (mn) | $M_j$ (kg) | $Y_j^i$ (%) |
|---|---|---|
| 0 | 0.38936 | 0 |
| 3 | 0.38772 | 0.42 |
| 6 | 0.38616 | 0.82 |
| 9 | 0.38433 | 1.29 |
| 12 | 0.38207 | 1.87 |
| 15 | 0.38028 | 2.33 |
| 18 | 0.37845 | 2.80 |
| 21 | 0.37666 | 3.26 |
| 24 | 0.37518 | 3.64 |
| 27 | 0.37413 | 3.91 |
| 30 | 0.37308 | 4.18 |
| 33 | 0.37211 | 4.43 |
| 36 | 0.37028 | 4.90 |
| 39 | 0.37028 | 4.90 |
| 42 | 0.36958 | 5.08 |
| 45 | 0.36911 | 5.2 |
| 48 | 0.36849 | 5.36 |
| 51 | 0.36802 | 5.48 |
| 54 | 0.36732 | 5.66 |
| 57 | 0.36689 | 5.77 |
| 60 | 0.36650 | 5.87 |

TABLE II

| $t_j$ (mn) | $K_1$ | $K_2$ | $L_1$ | $L_2$ | $\tau$ | $A^i$ (%) |
|---|---|---|---|---|---|---|
| 27 | 11.8044 | −5.30043 | −0.05086 | −0.08783 | 3.49360 | 6.5 |
| 33 | 9.83714 | −2.58834 | −0.02267 | −0.00718 | 4.47243 | 7.25 |
| 42 | 9.62450 | −3.43567 | −0.05130 | −0.11867 | 2.80437 | 6.19 |
| 54 | 8.94566 | −2.84182 | −0.05130 | −0.12922 | 3.09649 | 6.10 |
| 60 | 8.94706 | −2.78384 | −0.05015 | −0.12660 | 3.08637 | 6.16 |

What we claim is:

1. Apparatus for determining the moisture content of a material including:
   (a) means for heating a sample of the material under investigation, said means for heating including a micro-wave oven
   (b) means for weighing the sample in the course of heating and providing signals $M_j^i$ representing a series i of measurements of the weight of the sample at specific times $t_j$;
   (c) a processing unit including
      (i) a first computing means for converting the said signals $M_j^i$ into signals $Y_j^i$ representing the loss of weight of the sample in the course of heating and for computing, with the aid of the pairs of associated values $Y_j^i$, $t_j$ the n parameters of a general function $f_n(t)$ which is asymptotic with respect to t, and which represents the loss of weight of the sample in the course of time, and for computing the asymptotic value $A^i$ which is adopted by a specific function $f_n^i(t)$ when t tends towards infinity, said means for weighing being connected to said first computing means;

(ii) a second computing means for determining the differences $d^{i+1,i}$ between two asymptotic values $A^i$ and $A^{i+1}$ emanating from two successive series i and i+1 of measurements, said second computing means being connected to said first computing means; and (iii) a means for comparing the differences $d^{i+1,i}$ with a reference value representing the acceptable uncertainty regarding the moisture content of the material under investigation, said means for comparing being connected to said second computing means; and (d) means for restoring the asymptotic values when the differences reach values which are equal to or less than the reference value.

2. Apparatus according to claim 1, in which the general function $f_n(t)$ with n parameters to be determined is of the following analytical form:

$$\sum_{m=1,p} K_m [1 - \exp(t - \tau) L_m] \text{ where } K_m, L_m$$

and $\tau$ represent the n parameters to be determined, these parameters being constants specific to the material under investigation.

3. Apparatus according to claim 1, in which said processing unit is formed by a microprocessor.

* * * * *